United States Patent [19]
Larson et al.

[11] Patent Number: 6,114,558
[45] Date of Patent: Sep. 5, 2000

[54] PREPARATION OF ALKYL(AMINO) DIALKOXYSILANES

[75] Inventors: Gerald L. Larson, Newtown; Ram R. Chawla, Bensalem, both of Pa.

[73] Assignee: Sivento Inc., Ridgefield Park, N.J.

[21] Appl. No.: 08/998,134

[22] Filed: Dec. 23, 1997

[51] Int. Cl.$^7$ ........................................................ C07F 7/10
[52] U.S. Cl. .............................................................. 556/413
[58] Field of Search ............................................... 556/413

[56] References Cited

U.S. PATENT DOCUMENTS

| | | | |
|---|---|---|---|
| 4,650,891 | 3/1987 | Lennon | 556/480 |
| 4,672,135 | 6/1987 | Lennon | 556/480 |
| 4,888,436 | 12/1989 | Shiozawa et al. | 556/413 |
| 5,808,123 | 9/1998 | Balduf et al. | 556/413 |

*Primary Examiner*—Paul F. Shaver
*Attorney, Agent, or Firm*—Abelman, Frayne & Schwab

[57] ABSTRACT

Alkyl(amino)dialkoxysilanes are prepared by anhydrously reacting stoichiometric amounts of an alkoxysilane and an alkylaminomagnesium chloride in a reverse addition process. The alkylamino magnesium chloride is preferably prepared in situ by the reaction of a Grignard reagent (RMX) and an alkylamine in a suitable aprotic solvent, such as tetrahydrofuran. The "alkyl" substituent can be alkyl, arylalkyl or aryl. The reaction can be conducted in the temperature range of from 25° C. to 75 ° C., without a catalyst, and the aprotic solvent is recovered for re-use in the process.

18 Claims, No Drawings

PREPARATION OF ALKYL(AMINO) DIALKOXYSILANES

FIELD OF INVENTION

The present invention relates to an improved process for the preparation of alkyl(amino)dialkoxysilanes having an alkyl (or an aryl or arylalkyl), one amino substituent and two alkoxy groups attached directly to the silicon atom.

The preferred alkyl(amino)dialkoxysilane compounds have utility, inter alia, as highly-active stereoregulating catalysts, or catalyst components, in the α-olefin polymerization reaction to produce highly stereoregular polyolefins, e.g., α-olefin homopolymers and copolymers.

BACKGROUND OF THE INVENTION

It is known from the prior art that alkyl(amino) dialkoxysilanes can be prepared in relatively pure form. However, the known methods involve difficult syntheses in which the reaction parameters must be carefully controlled to minimize unwanted by-products and concomitant separation and activity problems. For example, U.S. Pat. No. 4,491,669 discloses the different approaches of (1) alcoholysis of a chlorosilane compound to replace one or more of the chlorine groups with alkoxy or aryloxy groups, and then replacing the remaining chlorine by reaction with a twice molar excess of an amino compound; and (2) by replacing one or more amino groups of a multiple-amine substituted silane compound by reaction with an alcohol. These reactions can be represented by the following simplified general equations:

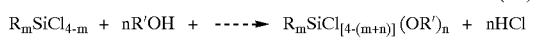
(1A)

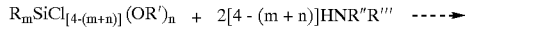
(1B)

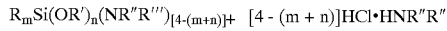

and

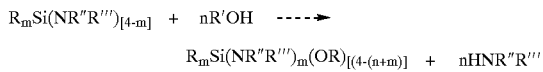
(2)

where:
R is hydrogen, a short chain alkyl or alkenyl group of up to eight carbon atoms or an aryl, such as phenyl;
R" and R'" are separately either hydrogen, a short chain alkyl or aryl, at least one being other than hydrogen;
R' is a short chain alkyl or aryl; and
m and n are integers.

These compounds have also been prepared by the reaction of an alkylamine with alkoxychlorosilane compounds. The reaction (1B) of an alkyltrichlorosilane with two equivalents of alcohol followed by displacement of the remaining chloride by an amine is of limited interest as a commercial process because of the difficulty in forming the alkylchlorodialkoxysilane (1A) without also forming alkyltrialkoxysilane and alkyldichloroalkoxysilane. This mixture of products affects the efficiency of the next reaction (1B). Similarly, the selective alcoholysis of an alkyltri(amino) silane (2) also results in a mixture of products and the attendant separation problems.

A process for producing alkyl(amino)dialkoxysilanes using a Grignard reagent in diethyl ether solvent is disclosed in Japanese patent application HEI 9[1997]-40714/HEI 7[1995]-192793. However, no yields were reported in any of the purported working examples of that application. When replication of the reported results was attempted, it was found that the piperidinomagnesium chloride salt and a diethylaminomagnesium chloride salt, (both prepared in accordance with the procedure described in Example 11 of the Japanese reference), were both insoluble in the diethyl ether. A slurry of the piperidinomagnesium chloride in diethyl ether was reacted with methyltrimethoxysilane to produce the expected methyl(piperidino)dimethoxysilane. This reaction proceeded very slowly. The 75% yield of crude product obtained is equivalent to about a 65% isolated yield (estimated) of the purified product. The results of the replication lead one of ordinary skill in the art to conclude that the processes described in this Japanese application would not be economically practical for use in a scaled-up, commercial process due to the relatively low yield of the desired product coupled with extremely long reaction time.

In view of these limitations of the prior art, it is a principal object of the present invention to provide an improved one-step process starting from alkylalkoxysilanes for producing alkyl(amino)dialkoxysilanes of high purity and in yields greater than those attained by the prior art. In the context of the description of the invention in this application, it is to be understood that the term "alkyl" means alkyl, arylalkyl and aryl substituents.

Another principal object of the invention is to provide an improved process that is practical and economical for the commercial production of the desired products by minimizing the production of unwanted by-products and the concommitant separation and activity problems.

It is another object of the invention to provide an improved process for producing alkyl(amino) dialkoxysilanes at temperatures ranging from 25–75° C.

An additional object of the invention is to provide an improved process for producing alkyl(amino) dialkoxysilanes in which the by-products are an alkane and a magnesium alkoxychloride salt which are non-hazardous and can be disposed of economically.

Still another object of the invention is to provide a process for producing alkyl(amino)dialkoxysilanes in which the solvent is recycled for use in the process.

A further object of the invention is to provide a process for producing specified alkyl(amino)dialkoxysilane compounds for use as stereoregulators in α-olefin polymerization catalysts.

SUMMARY OF THE INVENTION

In accordance with the improved process of the invention alkyl(amino)dialkoxysilanes of the general formula

(1)

(where the substituents R, $R^1$, $R^2$ and $R^3$ are defined below), are prepared by the reverse addition reaction of an alkylalkoxysilane with an alkylaminomagnesium chloride, which salt, in a preferred embodiment of the invention, is prepared in situ by the reaction of a Grignard reagent (RMgX) with an amine in an aprotic solvent in which the salt is completely soluble.

This preferred reaction scheme can be represented as follows:

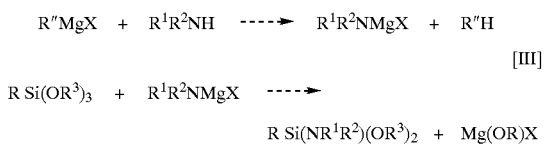

where:
- R and R" are straight or branched chain alkyl of 1 to 20 carbon atoms, arylalkyl or aryl radicals;
- $R^1$ and $R^2$ are alkyl radicals of 1 to 6 carbon atoms and one of them can be hydrogen;
- $R^3$ is an alkyl radical of 1–6 carbon atoms with methyl being preferred; and
- X is a halogen atom selected from Cl, Br or I, with Cl being preferred.

From the above, it is evident that the present invention includes aryl and aryloxy(amino) silanes, but for ease of reference the term "alkyl(amino)dialkoxysilanes" will be understood to mean both aryl and alkyl and (amino)aryl- and (amino)alkoxysilane compounds, unless the context indicates otherwise.

It is important that the process steps be practiced under anhydrous conditions since the presence of water will degrade the Grignard reagent, and will cause undesirable side reactions and the formation of by-products that constitute impurities in the finished product. Reaction vessels can be purged with dry nitrogen that is withdrawn under vacuum. Nitrogen can also be admitted to the reaction vessel during the reaction to ensure that atmospheric moisture is excluded. The reactants are also treated and/or handled to eliminate water prior to their addition to the reaction vessel.

As noted above, in the preferred embodiment of the invention, the process is directed to the production of an alkyl(amino)dialkoxysilane. In accordance with this aspect of the invention, the alkoxysilane is added slowly to the vessel containing the alkylaminomagnesium chloride that is fully dissolved in the stirred aprotic solvent. In accordance with the improved process, and the use of a solvent in which there is total solubility of the reagents, only one of the alkoxy groups is displaced from the silane, thereby providing the maximum yield of the desired alkyl(amino)dialkoxysilane.

In order to maximize both the purity and yield and to minimize reaction time, it is necessary to employ an aprotic solvent in which the alkylaminomagnesium chloride is completely soluble. In this regard, tetrahydrofuran (THF) has been found to be suitable and is particularly preferred. It has also been found that diethyl ether (ethyl ether) is not useful as a solvent, since many of the alkylaminomagnesium chloride compounds of interest are sparingly soluble in diethyl ether. Identification of suitable aprotic solvents in addition to THF can be made by routine experimentation, i.e., conducting the Grignard reaction and observing the solvent for the presence of a precipitate, either immediately, or over time, e.g., twelve hours. The complete and permanent solubility of the alkylaminomagnesium chloride is particularly critical in the practice of the process of the invention on a commercial scale, since the residence time of the reactants in the solvent will be much greater due to the increased volumes of the respective reactants.

If compounds of the general formula (I) are to be used as catalysts for the manufacture of stereoregular polyolefins by polymerizing α-olefins, it is preferred that only a single amino constituent be present. Commercially acceptable product for use as a catalyst or catalyst component will have a purity greater than 95%, and preferably 99%.

EXAMPLE 1

Preparation of Methyl(t-butylamino) dimethoxysilane

A thermometer an addition funnel and a condenser were fitted to a stirrer-equipped one liter, four-necked flask. The flask was charged with one mol of isopropylmagnesium chloride in 500 ml of tetrahydrofuran (THF). The addition funnel was charged with 1.02 mol (75 g) of tert-butylamine which was slowly added to the stirred isopropylmagnesium chloride. The reaction was mildly exothermic and there was immediate evolution of propane gas. After completion of the addition (2 hours), the contents were refluxed for 30 minutes to complete the evolution of the gas. The reaction mixture was cooled to room temperature and one mol (135 g) of methyltrimethoxysilane was added to the stirred reaction mixture over a period of one hour. The reaction was mildly exothermic and the contents were refluxed at a pot temperature of 75° C. for 30 minutes to complete the reaction. The methyl(t-butylamino)dimethoxysilane was filtered under nitrogen atmosphere from the magnesium methoxychloride. The salt cake was washed with diethyl ether (2×200 ml) to obtain the residual methyl(t-butylamino)dimethoxysilane. The solvent was distilled to a pot temperature of 90° C. and the residue was distilled under reduced pressure to yield 138 g of methyl(t-butylamino)dimethoxysilane as a colorless oil (purity>98%); bp 107° C./135 mm. The yield was 82% of theoretical.

EXAMPLE 2

Preparation of 3,3,3-Trifluoropropyl(2-ethylpiperidino)dimethoxysilane

Following the same general procedure described on Example 1, a flask was charged with one mol (218 gm) of 3,3,3-trifluoropropyltrimethoxysilane was added to one mol of 2-ethylpiperdinylmagnesium chloride, the salt having been prepared in situ by adding 2-ethylpiperidine (120 g, 1.05 mol) to isopropylmagnesium chloride (1 mol) in 500 ml of tetrahydrofuran. The reaction was mildly exothermic and the temperature rose to 45° C. at the end of the addition time of one hour. The reaction mixture was refluxed at the pot temperature of 70° C. for one hour and then cooled to room temperature. The 3,3,3-trifluoropropyl(2-ethylpiperidino) dimethoxysilane was filtered under nitrogen atmosphere from the magnesium methoxychloride. The filter cake was washed with ether (2×200 ml) to obtain the residual product. The solvent was removed by distillation to a pot temperature of 100° C. The residue was distilled under vacuum to yield 263 g of 3,3,3-trifluoropropyl(2-ethylpiperidino) dimethoxysilane as a colorless oil (purity>98%); bp 70° C./0.1 mm. The total yield was 88% of theoretical.

EXAMPLE 3

Preparation of Isobutyl(diethylamino) dimethoxysilane

Following the same general procedure described in Example 1, a flask was charged with one mol of isopropylmagnesium chloride in 500 ml of tetrahydrofuran under a dry nitrogen atmosphere and stirred. To this was added 1.05 mol (76.8 g) of diethylamine over a period of one hour. During the addition of the diethylamine to the reaction mixture, the pot temperature was maintained at 40–45° C. After the addition was complete, the reaction mixture was refluxed for 30 minutes to complete the evolution of the gas. The reaction mixture was cooled to a pot temperature of 50° C. and one mol (178 g) of isobutyltrimethoxysilane was added over a period of one hour. The reaction mixture was refluxed at a pot temperature of 75° C. for four hours to complete the reaction. The isobutyl(diethylamino) dimethoxysilane was filtered under a nitrogen atmosphere from the magnesium methoxychloride salt. The salt cake was washed with ether (2×200 ml) to obtain the residual isobutyl(diethylamino)dimethoxysilane. The combined filtrate was distilled to a pot temperature of 100° C. to remove the lighter fraction and the residue distilled under reduced pressure to yield 153 g of isobutyl(diethylamino) dimethoxysilaie as a colorless oil (purity>98%); bp 104° C./30 mm. The total yield was 79% of theoretical.

EXAMPLE 4

Preparation of Ethyl(cyclohexylamino) diethoxysilane

Following the same general procedure described in Example 1, a 500 ml, four-necked flask fitted with a pressure equalizing funnel was charged with 0.5 mol of isopropylmagnesium chloride in 250 ml of tetrahydrofuran. Cyclohexylamine, 0.55 mol (52 g), was added over 30 minutes via a pressure equalizing funnel. The contents were refluxed for 15 minutes to complete the evolution of gas. Ethyltriethoxysilane, 0.5 mol (96 g) was added via the pressure equalizing funnel. The contents were refluxed at a pot temperature of 70° C. for two hours. Ethyl (cyclohexylamino)diethoxysilane was filtered under nitrogen atmosphere from the magnesium ethoxychloride. The filter cake was washed with ether (2×100 ml) to obtain the residual product. The solvent was removed via rotary evaporation. The residue was distilled under vacuum to yield 102 g of ethyl(cyclohexylamino)diethoxysilane as a colorless oil (purity>98%); bp 68° C./0.5 mm. The total yield was 83% of theoretical.

Following the same general procedures described in the above examples, the additional alkyl(amino)alkoxysilanes identified in Table I, below, were prepared. The purity and yields obtained for each compound are also set forth, along with those for Examples 1–4.

TABLE I

| COMPOUND | $^1$H-NMR - L(CDCl$_3$) | $^{13}$C-NMR L(CDCl$_3$) | Appearance | Purity | Boiling Point | Yield (isolated) |
| --- | --- | --- | --- | --- | --- | --- |
| (3-methylbutyl(ethylpiperidino)-dimethoxysilane | 3.5 (s, 3H), 3.1–2.8 (m, 3H) 1.7–1.2 (m, 11H), 0.9–0.8 (m, 9H), 0.6 (m, 2H) | 51.9, 50.3, 38.7, 32.1, 30.9, 29.5, 27.8, 23.4, 22.4, 20.0, 11.7, 8.4 | Colorless liquid | 97% | 96° C./0.8 mm | 83% |
| (3,3,3-trifluoropropyl)(2-trimethyl-silylpiperidino)dimethoxysilane | 3.5 (s, 6H), 3.1–2.9 (m, 1H), 2.8–2.6 (m, 2H), 2.2–2.0 (m, 2H), 1.8–1.35 (m, 5H), 1.32–1.15 (m, 1H), 0.9–0.7 (m, 2H), 0.1 (s, 9H) | 127.7 (quartet J = 275 Hz), 50.1, 42.6, 42.2, 28.0 (quartet J = 30 Hz), 27.8, 23.4, 3.0, 0.2, −4.2 | Colorless liquid | 99% | 91° C./0.8 mm | 85% |
| (3,3,3-trifluoropropyl)(2-trimethyl-silylpyrrolidino)dimethoxysilane | 3.50 (s, 3H), 3.45 (s, 3H), 3.25–3.10 (m, 1H), 2.90–2.80 (m, 1H), 2.80–2.65 (m, 1H), 2.20–1.50 (m, 6H), 0.85–0.75 (m, 2H), −0.05 (s, 9H) | 129.6 (quartet J = 275), 50.1 (2 peaks due to ring isomers), 49 (2 peaks due to ring isomers), 47.6, 46.7, 28.2 (quartet J = 30), 28.0, 27.5, 2.9, −2.7 | Colorless liquid | 98% | 71° C./0.3 mm | 91% |
| n-propyl(cis-2,6-dimethyl-piperidino)dimethoxysilane | 3.4 (s, 6H), 3.3 (m, 2H), 1.8–1.2 (m, 8H), 1.1 (d, 6H), 0.9 (t, 3H), 0.5 (m, 2H) | 50.1, 44.1, 31.6, 24.6, 18.0, 16.8, 14.5, 13.3 | Colorless liquid | 96% | 69° C./0.4 mm | 86% |
| (3,3,3-trifluoropropyl)(decahydro-quinolino)dimethoxysilane | 3.5 (s, 6H), 3.1–2.7 (m, 3H), 2.2–1.9 (m, 3H), 1.8–1.1 (m, 12H), 0.9–0.7 (m, 2H) | 127.9 (quartet, J = 275 Hz), 52.6, 50.4 38.2, 36.9, 29.0, 28.5, 27.8 (quartet, J = 30 Hz), 26.4, 26.3, 20.5, 3.1 | Colorless liquid | 98% | 105° C./1.0 mm | 82% |
| (3,3,3-trifluoropropyl)(bis(2-ethyl-hexylamino)dimethoxysilane | 3.5 (s, 6H), 2.6–2.4 (dd, 4H), 2.2–2.0 (m, 2H), 1.6–1.1 (m, 18H), 1.0–0.7 (m, 14H) | 128 (quartet, J = 275 Hz), 50.4, 48.5, 39.4, 36.9, 30.8, 29.1, 28.2 (quartet, J = 30 Hz), 23.2, 14.2, 10.3, 3.2 | Colorless liquid | 95% | 200° C./1.4 mm | 83% |
| (3,3,3-trifluoropropyl)(2-ethyl-piperidino)dimethoxysilane | 3.49 (s, 6H), 3.08–2.97 (m, 1H), 2.93–2.89 (m, 2H), 2.2–2.0 (m, 2H), 1.76–1.43 (m, 7H), 1.43–1.25 (m, 1H), 0.87 (t, 3H), 0.82–0.75 (m, 2H) | 127.2 (q, J = 276 Hz), 52.2 38.8, 29.9, 28.8 (q, J = 30 Hz), 28, 23.5, 20.1, 11.6, 3.59 | Colorless liquid | 98% | 70° C./0.1 mm | 88% |
| (2-methylpropyl)(diethylamino)-dimethoxysilane | 3.47 (s, 6H), 2.87 (q, 4H), 1.88–1.74 (m, 1H), 1.03 (t, 6H), 0.96 (d, 6H), 0.59 (d, 2H) | 49.9, 28.7, 26.1, 24.2, 21.2, 15.5 | Colorless liquid | 98% | 104° C./30 mm | 79% |
| methyl(tert-butylamino)dimethoxy-silane | 3.45 (s, 6H), 1.17 (s, 9H), 1.05 (s, 1H), 0.05 (s, 3H) | 49.2, 48.1, 33.0, −5.0 | Colorless liquid | 98.5% | 107° C./135 mm | 82% |
| ethyl(cyclohexylamino)dimethoxy-silane | 2.76–2.65 (m, 1H), 1.90–1.50 (m, 5H), 1.37–0.79 (m, 6H), 1.18 (t, 4H) 0.96 (t, 3H), 0.54 (q, 2H) | 57.4, 49.2, 38.3, 24.6, 25.4, 18.0, 6.5, 3.7 | Colorless liquid | 98.2% | 68° C./0.5 mm | 83% |

The alkyl(amino)dialkoxysilane compounds produced by the improved process of the invention can be employed directly without the need for further purification as polymerization catalyst components. In particular, compounds containing dimethoxy radicals exhibit good activity in producing highly stereoregular α-olefin polymers.

The economic and processing advantages associated with the commercial production of alkyl(amino)dialkoxysilanes at a purity greater than 98% in accordance with the process of the invention will be apparent to one familiar with the art. Equally important from an overall economic and environmental standpoint are the relatively higher yields of products obtainable using the process of the invention and the ability to quantitatively recover the principal aprotic solvent in a form that permits its re-use in the process.

The present invention can be embodied in other specific forms without departing from its spirit or essential attributes, and accordingly, in determining the scope of the invention, reference is to be made to the following claims in association with the specification.

We claim:

1. An improved method for the preparation of alkyl (amino)dialkoxysilanes of the structure (I)

$$RSi(R^1R^2N)(OR^3)_2 \quad (I)$$

by the reaction (III):

$$R_nSi(OR^3)_3 + R^1R^2NMgX \longrightarrow RSi(R^1R^2N)(OR^3)_2 + Mg(OR^3)X \quad (III)$$

where:
R is a straight or branched-chain alkyl of from 1 to 20 carbon atoms an arylalkyl or an aryl radical;
$R^1$ and $R^2$ are alkyl radicals of from 4 to 6 carbon atoms, and one of them can be hydrogen;
$R^3$ is a straight or branched-chain alkyl of from 1 to 6 carbon atoms, an arylalkyl or an aryl radical;
X is chlorine, bromine or iodine; and
said improved method is characterized by the steps of:
mixing approximately stoichiometric amounts of R"MgX and $R^1R^2$NH in an anhydrous aprotic solvent in which the R"MgX is completely soluble,
where: R" is alkyl and $R^1$ and $R^2$ are as defined above;
reacting the alkylmagnesium halide and amino compound in accordance with (II):

$$R"MgX + R^1R^2NH \longrightarrow R^1R^2NMgX + R"H; \quad (II)$$

completing the reaction (II) by the timed addition of the alkyltrialkoxysilane;
removing the solvent by distillation; and
recovering the alkyl(amino)dialkoxysilane (I) having a purity in excess of 95%.

2. The method of claim 1 where the aprotic solvent is tetrahydrofuran.

3. The method of claim 1 where reactions (II) and (III) are conducted in a temperature range of from about 25° C. to 75° C.

4. The method of claim 1 where X is Cl.

5. The method of claim 1 where the yield of alkyl(amino) dialkoxysilane is at least about 79% of the theoretical yield for reaction III.

6. The method of claim 1 where $R^3$ is selected from the group consisting of methyl or ethyl radicals.

7. The method of claim 1 where the amino constituent is a piperidino group.

8. The method of claim 1 where the aprotic solvent is recovered for re-use in the process.

9. The method of claim 1 where the reaction products of reaction (II) are refluxed to remove the by-product R"H in the form of a gas.

10. The method of claim 1 where the reaction (II) is conducted in a nitrogen atmosphere.

11. A method for the preparation of alkyl(amino) dialkoxysilanes of the structure (I)

$$RSi(R^1R^2N)(OR^3)_2 \quad (I)$$

by the reaction (III):

$$R_nSi(OR^3)_3 + R^1R^2NMgX \longrightarrow RSi(R^1R^2N)(OR^3)_2 + Mg(OR^3)X \quad (III)$$

where:
R is a straight or branched-chain alkyl of from 1 to 20 carbon atoms an arylalkyl or an aryl radical;
$R^1$ and $R^2$ are alkyl radicals of from 4 to 6 carbon atoms, and one of them can be hydrogen;
$R^3$ is a straight or branched-chain alkyl of from 1 to 6 carbon atoms, an arylalkyl or an aryl radical;
X is chlorine, bromine or iodine; and
said improved method is characterized by the steps of:
mixing approximately stoichiometric amounts of R"MgX and $R^1R^2$NH in anhydrous tetrahydrofuran,
where: R" is alkyl and $R^1$ and $R^2$ are as defined above;
reacting the alkylmagnesium halide and amino compound in accordance with (II):

$$R"MgX + R^1R^2NH \longrightarrow R^1R^2NMgX + R"H; \quad (II)$$

completing the reaction (II) by the timed addition of the alkyltrialkoxysilane;
removing the tetrahydrofuran by distillation; and
recovering the alkyl(amino)dialkoxysilane (I) having a purity in excess of 95%.

12. The method of claim 11 where reactions (II) and (III) are conducted in a temperature range of from about 25° C. to 75° C.

13. The method of claim 11 where X is Cl.

14. The method of claim 11 where the yield of alkyl (amino)dialkoxysilane is at least about 79% of the theoretical yield for reaction III.

15. The method of claim 11 where $R^3$ is selected from the group consisting of methyl or ethyl radicals.

16. The method of claim 11 where the amino constituent is a piperidino group.

17. The method of claim 1 where the tetrahydrofuran is recovered for re-use in the process.

18. The method of claim 1 where the reaction products of reaction (II) are refluxed to remove the by-product R"H in the form of a gas.

* * * * *